United States Patent [19]

Hall

[11] 4,355,538

[45] Oct. 26, 1982

[54] EXO-ELECTRON NON-DESTRUCTIVE TEST DEVICE AND METHOD

[75] Inventor: Edward N. Hall, Rolling Hills Estates, Calif.

[73] Assignee: Chromalloy American Corporation, St. Louis, Mo.

[21] Appl. No.: 238,478

[22] Filed: Feb. 26, 1981

[51] Int. Cl.³ .............................................. G01N 3/32
[52] U.S. Cl. ........................................ 73/811; 73/577
[58] Field of Search ................ 73/799, 800, 808, 810, 73/812, 811, 577; 250/365, 372, 526

[56] References Cited

U.S. PATENT DOCUMENTS 4,175,447  11/1979  Fukuhara ............................. 73/799
4,283,956  8/1981  Lechner et al. ....................... 73/799

Primary Examiner—Jerry W. Myracle
Attorney, Agent, or Firm—Haverstock, Garrett & Roberts

[57] ABSTRACT

A non-destructive testing device and method is provided wherein a test piece is held in a test stand located in a test enclosure. The test enclosure is evacuated. The test stand and test piece held therein is then vibrated, immediately after which the test piece is irradiated by at least one beam of collimated radiant energy, preferably ultraviolet light, which is scanned over the test piece in a systematic pattern. Measurements of exo-electrons given off by the test piece responsive to the irradiation of the test piece are recorded for correlation with other exo-electron measurements made of the test piece throughout the life of the test piece. For metal test pieces not sensitive to this technique, a selected gas or gases (mixed or in sequence) may be introduced into the evacuated chamber for forming a surface compound of gas and metal on the surfaces of the test piece. The test enclosure is then evacuated and the test piece is vibrated and scanned by radiant energy and measurements taken.

20 Claims, 2 Drawing Figures

EXO-ELECTRON NON-DESTRUCTIVE TEST DEVICE AND METHOD

BACKGROUND OF THE INVENTION

The present invention relates to non-destructive measurements of metal fatigue and more particularly to a device and method for making non-destructive measurements of metal fatigue using exo-electrons.

DESCRIPTION OF THE PRIOR ART

High strength crystalline materials, including many metals and alloys, suffer deterioration of strength because of fatigue of the material with repeated cycles of stress variation. For many machine elements this fatigue phenomenon establishes the useful life of a part. In much highly stressed modern equipment, such as blades and disks of gas turbines, failure of such parts can be both very expensive and dangerous. To avoid such failures arbitary limits have been set for the useful life of such equipment, derived from studies of stresses experienced and number of stress reversals encountered at failure.

With no such arbitary limits established, life of such highly stressed parts before fatigue failure would vary widely, reflecting inhomogeneities in geometry and composition induced in manufacture, as well as anisotropies and surface defects characterizing the specific part in question. The arbitary limits set for such parts relate to the poorest parts expected to be found in service, thus minimizing failure probability. As a result of these arbitary limits, many perfectly good parts are discarded prematurely.

Because many machine elements of this character are exceedingly expensive, rejection of parts on such arbitary limits is very costly. The development of a non-destructive test procedure capable of indicating safe life remaining of a component would be extremely valuable for such very high cost parts. Although gas turbine blades and disks fall into this catagory, the procedures described herein are applicable to a wide variety of dynamically loaded machine elements.

Since the turn of this century, many phenomena promising to permit assessment of safe fatigue life remaining have been investigated. Among them are dye-penetrants, eddy current, ultra-sonics, radiography, positron loss, holography, and exo-electron emission. Despite substantial and growing activity in these fields, particularly during the last thirty years, no non-destructive test technique to establish safe component life remaining has emerged. In most of the approaches explored, flaws are only revealed when they have already assumed dangerous proportions. In others, correlation with potential failure has proved poor.

For the types of components under consideration, particularly gas turbine blades and disks, because of closely-controlled fabrication techniques employed, it is believed that dangerous fatigue failures are associated with surface defects. A useful non-destructive test, therefore, must identify sites of potential surface failure before they have formed cracks exceeding the length, depth, or shape known to be hazardous.

It has been known for about half a century that when metals are exposed to light above a critical frequency, electrons referred to herein as exo-electrons are emitted. These exo-electrons have been called thermal electrons, tribological electrons, and photo electrons.

Extensive research by many investigators has indicated limited correlation between exo-electron emission rates associated with accurately defined active emission sites; and patterns of strain, light exposure, heat applied and ambient pressure. Until now, however, no effort has been made to establish a historical record of the exo-electron emission of a single test piece throughout its life. There has also been little effort devoted to determination of statistical correlation of combined exo-electron emission stimulation with emission patterns.

Investigators have established that fatigue of at least some alloys is accompanied by a number of effects bearing on the emission of exo-electrons, such as oxide layer cracking and flaking, dislocation migration and concentration, slip-step and local strain, resulting in surface chemical bond energy distortion. Some of these effects, including loss of oxide layer and local temperature rise, are transient, rapidly declining in intensity as oxides return and temperatures equilibrate. Others, like slip-step surface and surface bond energy distortion, remain stable for extended periods. Specific materials subjected to reasonably defined modes of repeated stress develop highly repeatable, narrowly defined patterns of exo-electron stimulation. These exo-electron stimulation patterns involve several of the mechanisms indicated above, and therefore are useable in many cases to indicate location of, and time to, impending failure. This is particularly true in the case of turbine blades and disks where the chemistry and fabrication history of units is carefully controlled, and the manner of stress cycling is reasonably defined and repeated when the turbine blades and disks are used within anticipated operating limits.

Unlike other methods of non-destructive testing, combined stimulated exo-electron emission can present a very early and continuing picture of developing fatigue failure which can be interpreted quantitatively. Long before failure occurs, and before surface cracks can be detected by existing techniques, a sample turbine blade, for example, after a relatively short period of operation, will reveal, under test conditions, highly specific, well-defined sites of impending fatigue. The significance of these sites as potential foci of fatigue failure is indicated by the quantitative rate of exo-electron release at each site. In addition to indicating prospective premature failure of inservice parts, such as inspection method is useable to explore fatigue resistant properties of new designs before placing them in service.

SUMMARY OF THE INVENTION

It is therefore a principal object of the present invention to teach the construction and operation of an improved non-destructive testing apparatus which uses exo-electron emission for collecting data related to fatigue in a test piece.

It is a further object of the invention to teach the construction of an improved non-destructive testing apparatus wherein a test piece is exposed to a variety of gases and a mixture of gases under varying pressures and vibration cycles.

It is another object of the invention to teach the construction of an improved non-destructive testing apparatus wherein exo-electrons are stimulated by systematically scanning the test piece with collimated radiant energy.

It is a further object of the invention to teach the construction and use of an improved non-destructive testing apparatus using exo-electrons emitted from a test piece wherein the exo-electrons are stimulated by radiant energy having frequencies from about 0.9 to about $1.3 \times 10^{15}$ hertz (900–1300 terahertz) for most ferrous alloys.

It is a further object of the invention to teach the construction of an improved non-destructive testing apparatus using exo-electrons emitted from a test piece wherein the exo-electrons are stimulated by radiant energy having frequencies less than the Einstein emission value of the metal of the test piece.

It is another object of the present invention to teach the recording and correlation of exo-electron emission from a test piece over its life to evaluate the possible failure of the test piece.

It is another object of the present invention to teach the construction and use of an improved non-destructive testing apparatus which reduces the cost of turbine blades, disks and similar parts of machines by providing a method wherein the expected failure of individual parts being tested may be predicted.

These and other objects and advantages of the present apparatus and method will become apparent after considering the following detailed specification in conjunction with the accompanying drawings.

DESCRIPTION OF THE PREFERRED EMBODIMENT

Figure 1:
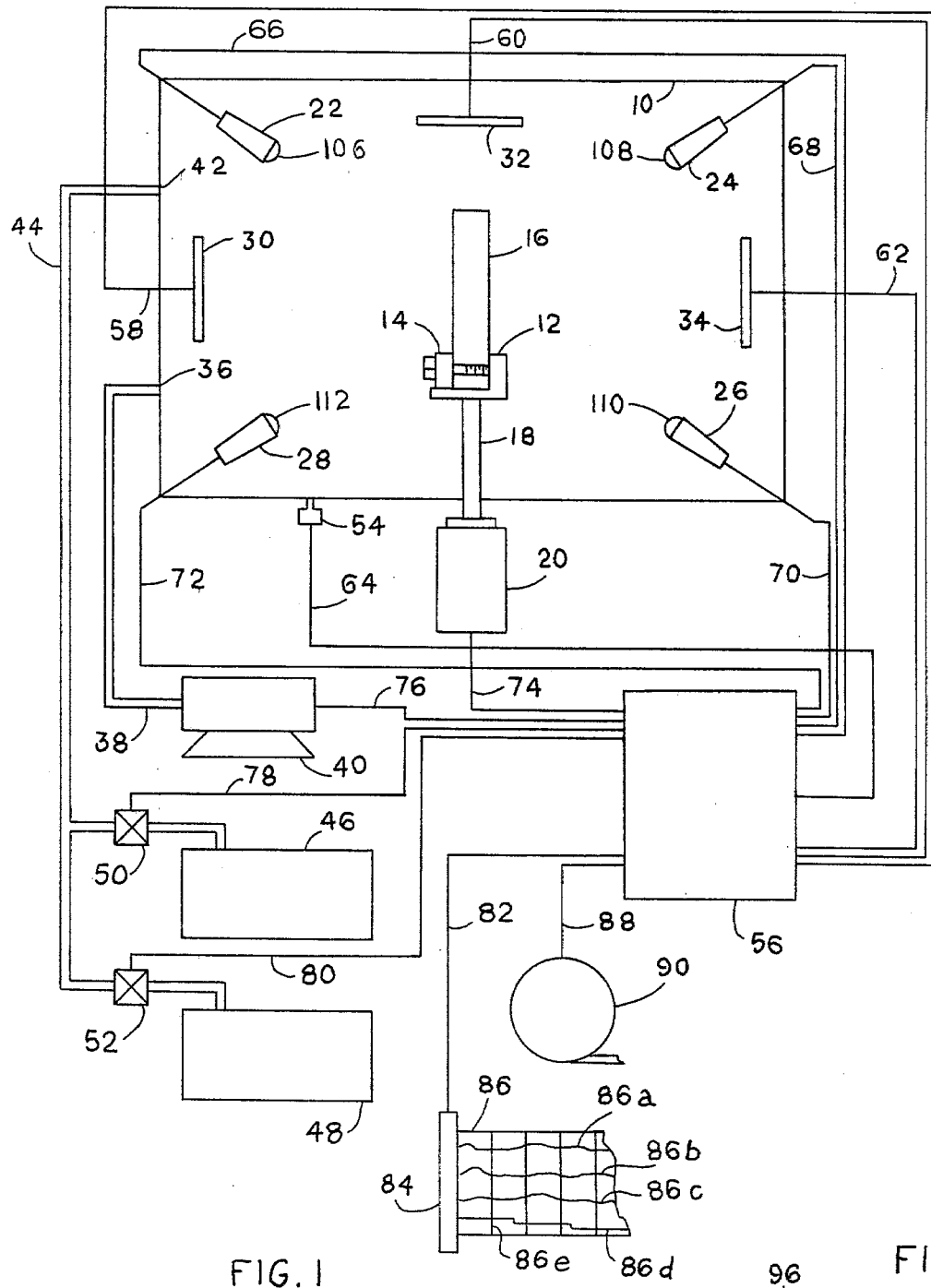
FIG. 1 is a diagrammatic representation of an embodiment of the non-destructive testing apparatus of the present invention.

Referring to the drawings more particularly by reference numbers, number 10 of FIG. 1 is an enclosure in which is located a test stand 12 having a clamping mechanism 14 for clamping a test piece 16 securely in place in the test stand 12. The test stand 12 is connected by a shaft 18 to a motor 20 for imparting vibrations to the test stand and the work piece 16 clamped therein. One or more scanning lights 22, 24, 26 and 26 are located in the enclosure and in the preferred embodiment include means for scanning the test piece 16 by collimated ultraviolet light beams in systematic patterns as the test piece is vibrated. Also located in the enclosure 10 are anodes 30, 32, and 34 for detecting exo-electrons given off by the test piece in response to the radiant energy emitted by the scanning lights 22-28. The anodes 30-34 have an electric potential which is about 100 volts to about 150 volts higher than the electrical potential of the test piece 16 clamped in the test stand 12. This electric potential is high enough to attract exo-electrons given off by the work piece 16 but low enough not to attract secondary electrons caused by phenomena other than exo-electrons emitted from test piece 16 in response to radiant energy from scanning light sources 22-28.

The enclosure 10 includes an exhaust 36 connected by a vacuum line 38 to a vacuum pump 40 for lowering the pressure of enclosure 10 and for flushing gas or mixtures of gases surrounding the test piece 16. The enclosure 10 also includes a gas inlet 42 connected by a gas line 44 to a series of storage tanks illustrated by tanks 46 and 48 for containing a variety of gases. These gases can include halogens, nitrogen, hydrogen, and gaseous hydrides of various metals such as boron. Passage of gasses from storage tanks 46 and 48 is controlled by electrically operated valves 50 and 52 respectively. Thus, valves 50 and 52 may be individually opened at different times, or opened together for various lengths of time to control the flow of either a pure gas or a mixture of gases from the storage tanks 46 and 48 through gas line 44 and gas inlet 42 into the enclosure 10 as desired.

The enclosure 10 also has a pressure transducer 54 for measuring the pressure which exists inside the enclosure 10.

The testing schedule is conducted by a test controller 56 preferrably a programmable electronic controller which may contain a process computer, a suitably programmed mini-computer or a micro-processor programmed as is known in the art. The anodes 30, 32 and 34 are connected to the test controller 56 by input leads 58, 60, and 62 respectively, and pressure transducer 54 is connected to the test controller 56 by an input lead 64. Output lines 66, 68, 70 and 72, each containing light controlling conductors, go from the test controller 56 to the scanning lights 22, 24, 26 and 28 respectively. The scanning lights units 22-28 are controlled by the test controller 56 to scan the test piece 16 with radiant energy, preferably ultraviolet light, in a set pattern as will be more fully explained in conjunction with FIG. 2. An output lead 74 goes from the test controller 56 to the vibrator motor 20 for vibrating the test piece 16 under the control of test controller 56. An output lead 76 connects the test controller 56 to the vacuum pump 40, and output leads 78 and 80 go from the test controller 56 to the electrically operated valves 50 and 52 respectively.

An output lead 82 goes from the test controller 56 to data logging equipment 84 which makes a visable record of the exo-electron responses sensed by anodes 30-34. The data logging equipment 84 may include various forms such as a recording oscilloscope or a pen recorder. In the embodiment shown in FIG. 1, the data logging equipment 84 is shown as a pen recorder which produces a data chart 86 having recorded thereon a plurality of data lines 86a, 86b, 86c and 86d. Lines 86a, 86b and 86c record the exo-electrons sensed by anodes 30, 32 and 34 respectively, while data line 86d records the pressure sensed by pressure transducer 84. Additional data lines may be added to the chart the status of the electrically operated valves 50 and 52 or other data as may be desired. The data chart 86 has vertical lines 86e representative of the elapsed time of the test schedule. By knowing the test schedule programmed into the test controller 56, the position of the test piece 16 and points of the test piece 16 being scanned by scanning lights 22-28 may be correlated to the responses of line 86a-86c. Thus, the chart 86 gives a three dimensional presentation of the exo-electrons emitted by test piece 16 in response to its irradiation by the radiant energy emitted by the scanning lights 22-28 throughout the testing schedule. An output lead 88 also goes from test controller 56 to a device for making a permanent record such as, for instance, by a computer compatible magnetic tape 90. The magnetic tape 90 and the chart 86 form a history of the individual test piece 16 being tested. Thus, the progress of the development of surface flaws or other inhomogeneities indicated by exo-electrons emitted by the test piece 16 may be followed long before such flaws would be observable by other testing techniques.

Figure 2:
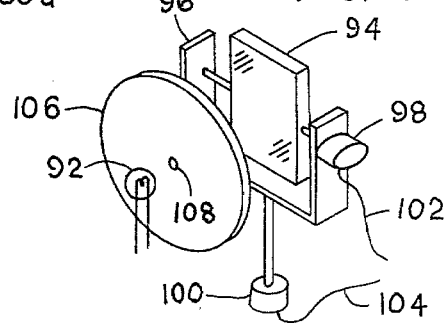
FIG. 2 is a perspective view of one embodiment of a scanning mechanism for use in the testing apparatus of FIG. 1 for scanning a work piece with collimated radiate energy.

Each scanning light 22-28 contains means for irradiating the work piece 16 with radiant energy, for example, ultraviolet light, in systematic patterns. FIG. 2 shows one embodiment of such a means wherein a mercury vapor or xenon discharge lamp 92 is positioned in front of a mirror 94 mounted on a gimbal 96. The position of the mirror 94 is determined by stepper motors 98 and 100 controlled by control leads 102 and 104 respectively. The exact frequency of the light emitted by the scanning lights 22-28 is determined by filters 106, 108, 110 and 112 (FIG. 1) such as a filter identified as Corning 954 available from Corning Glass Works, Inc. of Corning, New York, through which the light is directed. The radiant energy can thus be varied to have a frequency in the range of about 0.9 to $1.3 \times 10^{15}$ hertz and preferably to be just below the Einstein photo-emission value of the metal being tested. A light emitting diode may be used in place of the gas discharge lamp 92. Radiant energy emitted from the light source 92 is reflected from mirror 94 to the work piece 16 through the appropriate filter. The exact position where the radiant energy reflected from mirror 94 strikes the work piece 16 is controlled by the operation of motors 98 and 100. The light source 92 may be mounted on a frame connected to mirror 94 or may be located at a fixed location in front of the mirror 94 as desired. A means for collimating the light from the source 92 is shown between the source 92 and the mirror 94 and may be in the form of a disk 106 having an aperture 108 therein for passing only a narrow collimated beam of light to the mirror 94 to be reflected to the test piece 16.

In operation, the test piece 16 is clamped onto test stand 12 by the clamping mechanism 14 and the enclosure 10 is sealed. The testing schedule is then controlled by the test controller 56 which first energizes the vacuum pump 40 to remove the gases in the test enclosure 10 until the pressure is lowered to the desired value preferably less than about $10^{-3}$ torr. The test controller 56 monitors the pressure in enclosure 10 by signals from pressure transducer 54 over lead 64. When the proper pressure lever is reached, the test controller 56 stops the vacuum pump 40 by appropriate signals over lead 76 and starts the testing procedure. The test controller 56 vibrates the test piece 16 by energizing the motor 20 for a predetermined time and frequency. Immediately following this, the controller 56 begins the scanning of scanning lights 22-28 by appropriate signals over conductors corresponding to leads 102 and 104 in each of the output lines 66-72.

Reactive or inert gases may be added to test enclosure either individually or mixed with one another by the operation of electrically operated valves 50 and 52. The mixture and concentration of the gases is controllable by the length of time which the valves 50 and 52 are opened and by the operation of the vacuum pump 40, all under the control of the test controller 56. The pressure in enclosure 10 may also be varied as desired. The work piece 16 is subjected to one cycle of vacuum, vibration, and scanning, by radiant energy; and a recording is made as described. A selected gas, or gases is them admitted until a specified pressure is reached in enclosure 10. This pressure is maintained for an established period of time allowing the formation of gas-metallic compounds on the metal surfaces. At the end of this period the enclosure 10 is again evacuated and the test piece 16 is vibrated in the manner indicated previously. The test piece 16 is again scanned by radiant energy and a recording is made. In some cases a reducing gas such as hydrogen may be used to clean the surfaces of the test piece 16 prior to admission of a reactive gas. The responses of the anodes 30-34 and other desired parameters are recorded by the test controller 56 on the recording device 54 and stored on the recording medium 90 during the course of the test. The test controller 56 is programmed for the types of test pieces 16 being tested, the metal or material of which the test piece 16 is formed and the test schedule to be followed. The results of each test having been recorded, may be correlated with later tests run on the same test piece such that changes in the exo-electron emission can be noted and their development followed.

Thus there has been shown and described a novel non-destructive testing device and method of use which fulfill all of the objects and advantages sought therefor. It will be apparent to those skilled in the art, however, that many changes, modifications, variations, and other uses and applications for the subject device are possible. AAll such changes, modifications, variations and other uses and applications which do not depart from the spirit and scope of the invention are deemed to be covered by the invention which is limited only by the claims which follow.

What is claimed is:

1. A non-destructive testing device comprising:
   a test enclosure;
   holding means in said enclosure including means for removably holding a test piece to be tested;
   vibratable means connected to said holding means for vibrating said holding means and a test piece held thereby;
   radiant energy emitting means in said enclosure for irradiating a test piece in said holding means;
   measuring means in said enclosure for measuring electrons given off by a test piece held in said holding means responsive to the irradiation of said test piece by said radiant energy emitting means; and
   means for controllably introducing a gas into said enclosure.

2. The non-destructive testing device of claim 1 wherein said radiant energy emitting means emits radiant energy having frequencies of from about 900 to about 1300 terahertz.

3. The non-destructive testing device of claim 1 further comprising scanning means operable to control the irradiation of said test piece including means for scanning said test piece with radiant energy from said radiant energy emitting means in a systematic pattern.

4. The non-destructive testing device of claim 3 further comprising means for collimating the radiant energy emitted by said radiant energy emitting means.

5. The non-destructive testing device of claim 1 wherein said means for introducing gas includes means for introducing a gas selected from a group consisting of halogens, nitrogen, hydrogen, gaseous hydrides of metals, and mixtures thereof.

6. The non-destructive testing device of claim 1 wherein said measuring means includes; anode means in said enclosure, and means for electrically energizing said anode means and a test piece held in said holding means wherein said anode means has an electric potential from about 100 to about 150 volts higher than the electric potential of a test piece held in said holding means.

7. The non-destructive testing device of claim 1 further comprising means for varying the pressure within said enclosure.

8. The non-destructive testing device of claim 7 wherein said means for controlling the pressure within said enclosure maintains the pressure at a value not to exceed about $10^{-3}$ torr.

9. The non-destructive testing device of claim 1 further comprising recording means connected to said measuring means for recording the measurement of said measuring means.

10. A method for non-destructive testing of a metallic test piece comprising:
mounting a piece to be tested in a test chamber;
evacuating said test chamber;
introducing a selected gas into said test chamber;
allowing a gas-metallic compound to form on the surfaces of said test piece;
evacuating said selected gas from said test chamber;
vibrating said test piece;
irradiating said test piece with radiant energy; and
measuring exo-electrons given off by said test piece responsive to said irradiating step.

11. The method of claim 10 wherein said radiant energy is collimated.

12. The method of claim 11 wherein said irradiating step includes scanning said test piece with said collimated radiant energy in a systematic pattern.

13. The method of claim 12 further comprising correlating said scanning step and said vibrating step for identifying the point on said test piece being irradiated by said radiant energy.

14. The method of claim 13 further comprising recording the exo-electron measurements of said measuring step for correlating with other exo-electron measurements of said test piece.

15. The method of claim 10 wherein said major component of said radiant energy has a frequency within the range of about 900 to about 1300 terahertz.

16. The method of claim 15 wherein said frequency is just below the Einstein photo-emission value of the test piece material.

17. The method of claim 10 wherein said gas is selected from a group consisting of halogens, nitrogen, hydrogen, gaseous hydrides of metals, and mixtures thereof.

18. The method of claim 10 wherein said evacuating step includes reducing the pressure in said test chamber to a value of about $10^{-3}$ torr.

19. The method of claim 10 wherein said measuring step comprises;
providing anode means in said test chamber;
energizing said anode means with an electric potential sufficiently above said test piece to cause exo-electron current flow from said test piece to said anode means responsive to said radiant energy;
amplifying said exo-electron current flow from said test piece to said anode means giving an electric signal related to said exo-electron current flow, and
recording said electric signal.

20. The method of claim 19 wherein said electric potential is in the range of about 100 volts to about 150 volts.

* * * * *